United States Patent [19]

Cassou et al.

[11] Patent Number: 4,493,700

[45] Date of Patent: Jan. 15, 1985

[54] PROTECTIVE SHEATH FOR AN ARTIFICIAL INSEMINATION GUN, IN PARTICULAR FOR BOVINES

[76] Inventors: Robert Cassou, 1 rue Clémenceau; Maurice Cassou, Rue Clémenceau; Bertrand Cassou, Saint Symphorien des Bruyeres, all of 61300 L'Aigle, France

[21] Appl. No.: 425,287

[22] Filed: Sep. 28, 1982

[51] Int. Cl.[3] .................... A61M 1/00

[52] U.S. Cl. .................... 604/55

[58] Field of Search .................... 604/55, 54, 275, 263; 206/363, 364, 365, 438–440

[56] References Cited

U.S. PATENT DOCUMENTS 4,085,737 4/1978 Bordow .................... 604/263

4,237,882 12/1980 Wickham .................... 604/263 X

FOREIGN PATENT DOCUMENTS 1168607 4/1964 Fed. Rep. of Germany ........ 604/55

1284148 11/1968 Fed. Rep. of Germany ........ 604/55

*Primary Examiner*—John D. Yasko

*Attorney, Agent, or Firm*—Fidelman, Wolffe & Waldron

[57] ABSTRACT

The sheath is of the type having a thickness which is substantially constant throughout its length and having at a first end, or insemination end, a narrowed shape (4*b*).

The problem is to provide a sheath which may be employed on an insemination gun which fixes the sheath by means of projections without presenting difficulties when manufacturing or when inserting the sheath.

According to the invention, this sheath is characterized in that its opposite end portion (4*a*), or fixing end portion, of very short length relative to the total length of the sheath, has an inside diameter substantially larger than the constant inside diameter it has throughout the remainder of its length. The invention has an advantageous application in respect of sheaths for insemination guns for bovines.

4 Claims, 3 Drawing Figures

PROTECTIVE SHEATH FOR AN ARTIFICIAL INSEMINATION GUN, IN PARTICULAR FOR BOVINES

The present invention relates to cylindrical flexible and protective sheaths for use in cooperation with artificial insemination guns, in particular for bovines, of the type comprising a tubular body which is adapted to receive at one end a supply of semen in the form of a straw, and in which is slidably mounted a plunger-rod adapted to expel the semen from the straw, this body having at its other end a fixing portion which has external radial projections the height of which, as measured from the axis of the body, exceeds the inside radius of the fixing end portion of the unattached or free sheath, the flexible sheath having a constant thickness throughout its length and surrounding the assembly of the tubular body and the straw and being detachably maintained on said fixing portion of the body by an elastic gripping of the projections of the fixing portion, the sheath having at the other end a narrowed shape for supporting the free end of the straw acting as a supply of semen.

Sheaths of this type are known, for example from French Pat. No. 78 13 524, which are employed on guns and in which, in a particularly advantageous embodiment, the fixing portion has, in order to constitute said radial projections, one or more helical coils which project from the cylindrical surface of this fixing portion.

However, in these known guns, for purposes of machining, for example turning on automatic screw machines, in the case of said coils (operation which requires maintaining a minimum thickness for supporting the projections or coils to be formed), it is necessary to give to the whole of the cylindrical fixing portion a relatively large outside diameter which is in any case distinctly larger than that required by the other functions of the gun body: reception of the straw and the guiding of the plunger-rod. This fixing portion having radial projections is in particular constructed in the form of a hollow cylindrical member mounted around the tubular gun body proper. The sheaths employed heretofore were perfectly cylindrical, i.e. had a constant diameter throughout their length when not attached to the gun, and as a result of the aforementioned large dimensioning of the fixing portion of the body, this diameter of the sheath; which must only be slightly less than that of said fixing portion, on account of the degree of elasticity of the material normally employed for this sheath (usually polyvinyl chloride), is itself rather distinctly larger than that of the tubular body.

Consequently, users, generally inseminators, who are very numerous and have in stock large quantities of sheaths of an older model prior to the development of the arrangement disclosed in said patent and consequently having a distinctly smaller constant diameter, find that it is impossible to employ these older sheaths on the new model of the gun employing radial projections, such as coils, for fixing the sheath.

Now, in a large number of cases, these users are extremely desirous to employ sheaths of only a moderate diameter, since this facilitates the insertion of only the instrument in the genital passages of the animal and is even found to be absolutely essential in the case of young animals, such as heifers or young cows. Moreover, a second drawback resides in the manufacture of the sheaths by extrusion when their diameter is excessively large. Indeed, these sheaths must have at the end opposed to the fixing end a narrowed portion which imparts thereto a frustoconical shape which terminates in an inner ledge and which acts as a support for the end of the straw through which the semen must be expelled.

Now, in the machines employed for producing this narrow portion, an increase in the diameter of a few tenths of a millimeter is sufficient to require two successive strokes of the tool on the end of the sheath, since the larger amount of material corresponding to the considered increase in diameter is too large to enable the machine to produce, without difficulty (binding or corrugations) and in a single stroke the required shrinkage of the material, whereas this was possible in the construction of the sheaths of smaller diameter adapted to the gun model which existed before the construction including projections or coils taught in said Pat. No. 78 13 524. It will be recalled for information that in this prior model, for example conforming to French Pat. No. 2 358 136, the sheath had a relatively small diameter which was constant throughout its length and there was formed at its fixing end a slot which enabled it to be engaged on a frustoconical bearing portion of the gun body, this slotted portion being clamped against the bearing portion by a ring which was forced over the sheath.

Thus it will be understood that, although apparently unimportant to an inexperienced person, the aforementiond difference of a few tenths of a millimeter is well known to persons skilled in the artificial insemination art since the appearance of the new model of the gun according to Pat. No. 78 13 524, and that, since this time, no solution has been provided to the double problem involved in the use of a sheath of larger diameter, rendered necessary by the fixing by means of projections or coils, namely, on one hand, the resulting hinderance when inserting the gun in the genital passages of the animal and, on the other hand, the necessity of producing the required narrowing by two strokes.

This is why an object of the present invention is to provide a sheath which is adapted to be employed on a gun employing fixing means with projections or coils but which is also just as easy to insert as in the case of a gun of a previous model and which may be narrowed by a single stroke of a tool. The invention provides a cylindrical flexible protective sheath adapted to be employed with a gun of the type defined in the first paragraph of the present description, characterized in that its end portion which is adapted to be elastically clamped on the fixing portion of the gun body, and only this portion, has an inside diameter (when not attached to the gun) which is substantially larger than the constant inside diameter the sheath has throughout the remainder of its length which constitutes the major part and is adapted to surround the rest of the tubular body and the straw. With this arrangement, the setting of the end portion of narrowed shape can be produced in a single stroke and the user can achieve, much more easily with much less risk of harming the animal, the insertion of the major part of the instrument provided with its sheath in the genital passages since, according to the invention, the diameter thereof is the diameter of the conventional instruments and sheaths which existed prior to the Pat. No. 78 13 524.

According to a particularly advantageous embodiment of the invention, the fixing end of the sheath of larger diameter is formed by a portion produced by an expansion operation, such as a tube-expanding operation. It should be stressed in this respect, that, inasmuch as the sheaths are produced by extrusion, this type of forming operation results in slight variations of the diameter along the lenght of the sheath, with these variations remaining upon the cooling following this extrusion. Now, the tube-expanding type of operation here envisaged for producing the end portion of the sheath of larger diameter enables this portion to be given mechanically a perfectly precise inside diameter notwithstanding the initial variations due to the expansion, which results in a perfect adaptation of the end portion of the sheath on the fixing portion of the gun body and an excellent seal. Further, such a sheath may be produced on existing machines already employed for producing sheaths having a constant diameter throughout their length and slotted, such as previously taught by Pat. No. 78 13 524. Indeed, it is merely necessary to replace on such a machine the slotting tool by a rotating tube-expanding tool whereby it is possible to produce and conserve the end portion of larger diameter of the sheath.

Further features and advantages of the invention will be apparent from the ensuing description which is given merely by way of example with reference to accompanying drawings in which.

Figure 1:
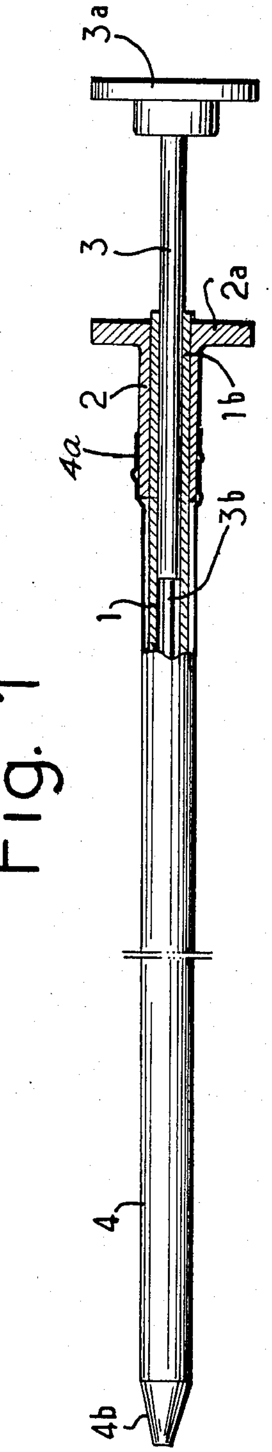
FIG. 1 is a partial sectional view of a gun provided with a sheath according to one embodiment of the invention.
Figure 2:
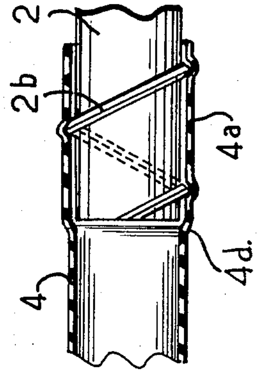
FIG. 2 is a partial sectional view, to an enlarged scale, of the portion of the sheath fixed on the gun.

The gun shown in FIG. 1 comprises a tubular body 1 provided with a head 2 for fixing the sheath and holding the gun, a plunger-rod 3 and a protective sheath 4.

Figure 3:
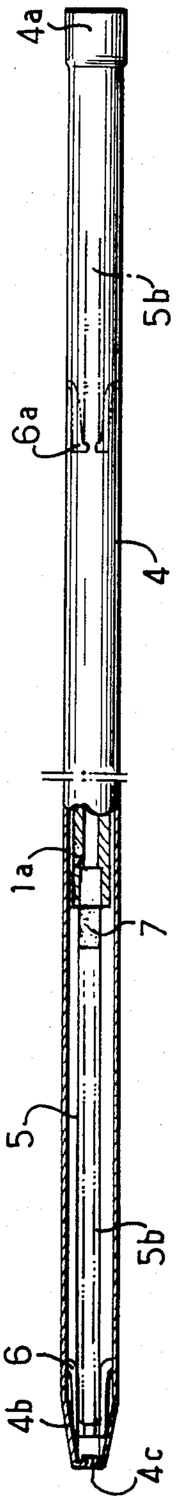
FIG. 3 is a sectional view of the protective sheath, with a part cut away in the centre in the direction of its length, it being understood that, at the scale at which it is represented, this length would be distinctly greater than the length of the drawing sheet. A similar cut-away portion is provided in FIG. 1 for the same reason and concerns not only the sheath but also the gun.

As shown in FIGS. 1 and 3, the tubular body 1 is a cylindrical member having a constant thickness throughout its length and having, on one hand, an end portion 1*a* (FIG. 3) for fixing the straw and an opposite end portion 1*b* for mounting the head 2. The latter is formed by a tubular attached member of short length which is fitted and secured on the end portion 1*b* of the body. At its outer end, this head has an annular radial plate portion 2*a* against which the fingers of the user bear. At its other end, extending toward the end 1*a* of the body, the outer cylindrical surface of this member 2 has a radial projection 2*b* in the form of a helical profile for example having the extent of two coils, the section of this projection being triangular and having a height in the radial direction of the order of a few tenths of a mm, e.g. 2/10 to 3/10 mm. This head 2 and the tubular body 1 are made from a rigid material such as stainless steel.

The protective sheath 4 is formed by a cylindrical sleeve produced, for example by extrusion from a flexible or semi-rigid material such as polyvinyl chloride. This sheath has a constant thickness throughout its length and this thickness is small as compared to the thickness of the body 1 and of the head 2 and is, for example, 2/10 mm, while the outside diameter of the cylindrical outer surface of the head 2 is for example of the order of 4 mm. This sheath has at one of its ends a short end portion 4*a* which is substantially a little longer than the region of the head carrying the spiral projection 2*b*, this end portion 4*a* having inside and outside diameters which are slightly larger than those of the body portion 4 of the sheath which is free from or unattached to the gun so that this portion 4*a* can be slipped without difficulty over the cylindrical surface of the member 2. This end portion 4*a* is advantageously a permanent set formed by a tube-expanding operation which imparts thereto a perfectly smooth inner surface. This end portion 4*a* is however narrow enough to enable it to grip radially the member 2 throughout the length of the spiral projection 2*b*.

Owing to this arrangement, i.e. the presence of this larger end portion, advantageously produced by a tube-expanding operation, the sheath 4 can be easily engaged on the fixing portion 2 of the gun by slightly giving in the radial direction to permit the embedding of the spiral projection 2*b* in its inner wall. Consequently, the body part 4 of the sheath has inside and outside diameters which are reduced by several tenths of a millimeter, for example of the order of 2/10 mm, thus affording an essential advantage over conventional sheaths which have throughout their length diameters which correspond to those of the presently described end portion 4*a*.

At its opposite end, the sheath 4 has a narrowed shape, for example produced by a setting or crimping operation which imparts thereto a frustoconical profile 4*b* which internally terminates in a folded-over ledge or flange 4*c*. The relatively small diameter of the body part 4 of the sheath permits the setting of this end portion 4*b* in a single stroke by means of conventional machines for producing sheaths by extrusion and setting designed for producing sheaths used on a type of gun which is quite different from that described hereinbefore and corresponds to constructions such as those of the French Pat. No. 2 358 136 in which there is no fixing of the sheath by means of a spiral projection on the head 2.

This set end portion 4*b* of the sheath provides for an end of a supply of semen or straw 5 the other end of which bears against an inner shoulder of the end portion 1*a* of the tubular body. There may also be provided in the known manner within the sheath 4 a small slidable sleeve 6 for reducing the diameter and providing a support for a thinner straw 5*b* shown in dot-dash lines and employed in some cases of insemination. This sleeve itself bears against the frustoconical portion 4*b* of the sheath when the straw is in the position of use. This sleeve is also shown in dot-dash lines in a standby position located in the vicinity of the end portion 4*a* of the sheath for receiving the straw of this type 5*b* when the latter is engaged in the sheath before the assembly comprising the sheath and the straw is fitted on the gun proper, constituted by the tubular body 1 and the plunger-rod 3.

The last-mentioned plunger-rod 3 is a solid rod which is slidably mounted in the tubular body 1 and has at its end, adjacent to the head 2, a small annular handling disc 3*a* which permits shifting the plunger-rod 3 by means of the thumb of the user, while at its opposite end it has a portion 3*b* of reduced diameter to enable it to be inserted in the straw 5 or 5*b* and thus act as an ejecting plunger for a piston-plug 7 normally provided inside the straw.

It will be observed that the shoulder 4*d* existing between the body part 4 of the sheath and its larger end portion 4*a* does not in fact bear against the front annular surface of the member 2, since, in practice, the inside diameter of this body part 4 may be slightly larger when unattached to the gun, by for example 2/10 mm, than the outside diameter of the cylindrical surface of the body 2, it being of course, on the other hand, less than the diameter of the crests of the coils 2*b* so as to allow the elastic gripping of the end portion 4*a* on these coils.

We claim:

1. A cylindrical flexible protective sheath insertable into an animal during use with an artificial insemination gun, the sheath having a substantially constant wall thickness throughout the length of the sheath and having an open insemination end portion of a narrowed shape and an opposite sheath-fixing end portion having a very short length relative to the total length of the sheath and a free inside diameter substantially larger than a constant free inside diameter that the sheath has between said end portions.

2. A sheath according to claim 1, wherein said sheath-fixing end portion of larger diameter is a permanent set resulting from an expanding operation, such as a tube-expanding operation.

3. An artificial insemination gun comprising a sheath as claimed in claim 1, a tubular portion presenting a first end for receiving a semen containing straw and for insertion into said sheath so as to locate said straw in said sheath at said insemination end of said sheath, and a second end on which is secured a ferrule presenting an outer cylindrical surface having radial projections therefrom, said free inside diameter of said sheath-fixing end portion of said sheath being intermediate between an outer diameter of said outer cylindrical surface and a larger diameter defined by a height of said radial projections, whereby said projections stretch and grip said sheath fixing portion when said tubular portion and ferrule are inserted in said sheath.

4. An artificial insemination gun comprising a sheath as claimed in claim 2, a tubular portion presenting a first end for receiving a semen containing straw and for insertion into said sheath so as to locate said straw in said sheath at said insemination end of said sheath, and a second end on which is secured a ferrule presenting an outer cylindrical surface having radial projections therefrom, said free inside diameter of said sheath-fixing end portion of said sheath being intermediate between an outer diameter of said outer cylindrical surface and a larger diameter defined by a height of said radial projections, whereby said projections stretch and grip said sheath fixing portion when said tubular portion and ferrule are inserted in said sheath.

* * * * *

UNITED STATES PATENT AND TRADEMARK OFFICE

CERTIFICATE OF CORRECTION

PATENT NO. : 4,493,700

DATED : 1/15/85

INVENTOR(S) : Cassou, et al.

It is certified that error appears in the above-identified patent and that said Letters Patent are hereby corrected as shown below:

On the title page between lines [22] and [51] add:

[30] Foreign Application Priority Data

April 6, 1982 [FR] France 82 05954

Signed and Sealed this

*Sixteenth* Day of *July 1985*

[SEAL]

*Attest:*

DONALD J. QUIGG

*Attesting Officer* *Acting Commissioner of Patents and Trademarks*